United States Patent [19]

Wetzel

[11] 4,213,981

[45] Jul. 22, 1980

[54] INJECTABLE ANESTHETIC

[75] Inventor: Jon C. Wetzel, Plattsburgh, N.Y.

[73] Assignee: American Home Products Corporation, New York, N.Y.

[21] Appl. No.: 941,999

[22] Filed: Sep. 13, 1978

Related U.S. Application Data

[63] Continuation-in-part of Ser. No. 787,643, Apr. 14, 1977, abandoned.

[51] Int. Cl.² ............... A61K 31/415, A61K 31/54
[52] U.S. Cl. .................................. 424/247; 424/273 R
[58] Field of Search .................. 424/273 R, 424/247

[56] References Cited

U.S. PATENT DOCUMENTS

| | | | |
|---|---|---|---|
| 3,330,826 | 7/1967 | Schmitt et al. | 424/247 |
| 3,567,831 | 3/1971 | Middleton et al. | 424/273 |

OTHER PUBLICATIONS

Chemical Abstracts 75:47209p (1971).

Primary Examiner—Jerome D. Goldberg

[57] ABSTRACT

A new anesthetic composition comprising a specified mixture of acepromazine or its pharmaceutically acceptable salts and midaflur is disclosed. This composition induces a useful surgical plane of anesthesia in mammals while substantially reducing troublesome side effects encountered with the use of midaflur by itself.

7 Claims, No Drawings

INJECTABLE ANESTHETIC

BACKGROUND OF THE INVENTION

1. Field of the Invention

This application is a continuation-in-part of Ser. No. 787,643, filed Apr. 14, 1977, and now abandoned.

This invention deals with a new and improved anesthetic composition for mammals. More specifically, this composition comprises a specified mixture of acepromazine or its pharmaceutically acceptable salts and midaflur. The novel compositions described herein reduce or eliminate side effects, such as involuntary leg movements and vocalization during their use in inducing anesthesia.

2. Prior Art

U.S. Pat. No. 3,567,831 and U.S. Pat. No. 3,459,766, incorporated herein by reference, both disclose 3-imidazoline 4-amino-2,2,5,5, tetrakis (trifluoromethyl) which is the chemical name for the compound generically known as midaflur. The compounds in these patents are described as having a depressing effect upon the central nervous system and the ability to decrease muscle tone. These properties are described as useful in causing relaxation in general anesthesia.

A paper entitled, "The Pharmacology and Toxicology of Midaflur" by R. Clark et al appearing in Toxicology and Applied Pharmacology 18,917–943 (1971) also describes the above-mentioned properties.

U.S. Pat. No. 3,330,826, incorporated herein by reference, describes acepromazine and its corresponding salts and describes these compounds as having local anesthetic properties equal or greater than those of chlorpromazine.

SUMMARY OF THE INVENTION

It has now been discovered that when midaflur is administered intravenously it induces a surgical plane of general anesthesia in mammals. However, troublesome side effects frequently occur during the induction period as well as the period of surgical anesthesia. It has now been found that when acepromazine or its pharmaceutically acceptable salts is administered with midaflur, side effects are reduced or eliminated. The amount of acepromazine or its pharmaceutically acceptable salts necessary to reduce or eliminate side effects varies from about 0.025 mg/kg to about 6.0 mg/kg of mammal body weight. The preferred range is from about 0.05 mg/kg to about 2.5 mg/kg. The ratio of midaflur to acepromazine or its pharmaceutically acceptable salts is from about two hundred to one to about one to one. The preferred ratio is from about one hundred to one to about two to one.

DESCRIPTION OF THE INVENTION

For purposes of this application the following terms will have the following meaning:

Induction Time—In all animal species with the exception of horses, this refers to the time from injection to the first time the pedal reflex was abolished or the first time the animal did not show any indication of a pain response (pigs and sheep only). In horses, the induction time refers to the time from injection to the first time the animal was in a position of lateral recumbancy.

Surgical Plane—For all species with the exception of horses, the surgical plane was defined as the time from injection until the last recorded time the pedal reflex was abolished or the animals showed no indication of a pain response (pigs and sheep only). In horses, the surgical plane was the time from injection to the last recorded time the animal was in lateral recumbancy.

Recovery Time—For all animal species, the recovery time was defined as the first time the animal stood after injection.

In addition to acepromazine or their pharmaceutically acceptable salts being used to eliminate the side effects of midaflur; chloropromazine, promazine, decamethonium bromide, d-tubocurarine chloride, diazepam or their pharmaceutically acceptable salts can be used to reduce or eliminate the side effects of midaflur. In a preferred embodiment of this invention the maleate salt of acepromazine is employed with midaflur. Electroencephalographic data indicates that acepromazine maleate potentiates midaflur's ability to depress brain activity.

The minimum effective dose of the preferred formulation of midaflur/acepromazine maleate in several animal species is as follows:

Dogs and Cats about 4.0/0.04 mg/kg of body weight
Sheep about 2.0/0.02 mg/kg of body weight
Horse about 1.0/0.01 mg/kg of body weight
Pigs about 1.5/0.015 mg/kg of body weight When this preferred formulation is administered to small animals such as dogs and cats the concentration of midaflur/acepromazine maleate is about 10.0–20.0/0-.2–0.4 mg/ml. Higher concentrations per ml would be utilized for larger animal use.

The compositions of this invention can be prepared by dissolving midaflur and acepromazine or its pharmaceutically acceptable salts in an appropriate solvent such as ethyl alcohol. Propylene glycol can be used in combination with ethyl alcohol. Water can also be added to these solvents. The compositions of this invention can be administered intravenously, intramuscularly, intraperitoneally and subcutaneously. For best results the compositions of this invention are administered intravenously to mammals. Examples of mammals on which the formulation of this invention have been used successfully include dogs, sheep, horses, pigs, cats and primates. The following examples illustrate the advantages of a midaflur-acepromazine maleate anesthetic composition over the individual components.

EXAMPLE 1

Two 20 mg/ml midaflur formulations were prepared in the manner essentially described below. These two formulations were prepared with the following components:

Midaflur Formulations
1 - 20.0 mg/ml
  1500 mg midaflur
  q.s. to 75.0 ml with 50% ethanol
2 - 20.0 mg/ml
  800 mg midaflur dissolved in 16.0 ml of 100% ethanol
  q.s. to 40.0 ml with sterile distilled water Both of these formulations were administered intravenously at various doses to dogs. The results are summarized in Table I which appears on the following page:

TABLE I

DOGS
THE EFFECT OF VARIOUS CONCENTRATIONS OF MIDAFLUR I.V. ON INDUCTION TIME, SURGICAL PLANE, RECOVERY TIME AND SIDE EFFECTS

| Formulation No. | 2 | 2 | 1 | 2 | 2 | 1 | 1 | 2 | 2 | 1 | 1 | 1 | 1 | 1 |
|---|---|---|---|---|---|---|---|---|---|---|---|---|---|---|
| Dose (mg/kg) | 2.0 | 2.0 | 5.8 | 6.0 | 6.0 | 8.0 | 8.0 | 8.0 | 8.0 | 9.0 | 12.0 | 12.0 | 16.0 | 16.0 |
| Concentration (mg/ml) | 20.0 | 20.0 | 20.0 | 20.0 | 20.0 | 20.0 | 20.0 | 20.0 | 20.0 | 20.0 | 20.0 | 20.0 | 20.0 | 20.0 |
| Induction Time (min) | — | — | 8 | 4–6 | — | 2 | 4 | 4 | — | 6 | 2 | 3 | 3 | 2 |
| Surgical Plane (min) | None | None | 22 | 45 | None | 77 | 43 | <23 | ? | 28 | <120 | 32 | <32 | 180 |
| Recovery (min) | >30 | 14 | 74 | 60 | 20 | 240 | 285 | 45 | >85 | 140 | 165 | >270 | 62 | >210 |
| Side Effects | | | | | | | | | | | | | | |
| A. Running Movements | a | a | 2 | 3 | a | 1 | 1 | 3 | Yes | 0 | 3 | 3 | 1 | 3 |
| B. Vocalization | a | a | 0 | 1 | a | 1 | 1 | 3 | Yes | 0 | 0 | 1 | 1 | 1 |
| Emesis | No | No | No | No | No | Yes | Yes | No | No | Yes | No | No | No | No | a = not applicable
Side effects refer to those side effects that occur from induction time until the end of the surgical plane where:
  0 = none
  1 = minimal, occurred during less than ¼ of the surgical plane
  2 = moderate, occurred during ¼ to ½ of the surgical plane
  3 = maximal, occurred during greater than ½ of the surgical plane As can be seen from the preceding table, ten of the fourteen dogs tested experienced running movements during the surgical plane, vocalization occurred with eight of the fourteen dogs at least 50 minutes after injection. Therefore, while midaflur does induce a surgical plane of anesthesia in dogs, there are troublesome side effects that do occur which limits the use of midaflur as an anesthetic.

EXAMPLE 2

Four different formulations (5–8) containing midaflur and acepromazine maleate were prepared. Additionally, Formulation 2, described in Example 1, was administered simultaneously in various dose levels via a "Y" shaped tube with each of two acepromazine maleate formulations having a concentration of 5 mg/ml (Formulation 3) and 10 mg/ml (Formulation 4) respectively. The preparation and components of Formulations 3 through 8 are represented below:

Acepromazine Maleate Formulation
3 - 5.0 mg/ml
   5.0 ml of a preserved pH adjusted aqueous Acepromazine Maleate Injectable Formulation (10.0 mg/ml)plus
   5.0 ml of sterile distilled water Acepromazine Maleate Injectable Formulation
4 - 10.0 mg/ml of a preserved pH adjusted aqueous injectable formulation.

Midaflur/Acepromazine Maleate Formulations
5 - 75.0/37.5 mg/ml
   7.500 g midaflur
   3.750 g acepromazine maleate
   35.0 ml absolute alcohol
   35.0 ml propylene glycol
   q.s. to 100.0 ml with distilled water Vehicle system (for Midaflur/Acepromazine Maleate formulation Nos. 6, 7, and 8)
A stock solution consisting of equal parts of:
propylene glycol
ethyl alcohol
distilled water

6 - 37.5/37.5 mg/ml
   1.875 g midaflur
   1.875 g acepromazine maleate
   q.s. to 50.0 ml with vehicle system
7 - 37.5/18.75 mg/ml
   3.750 g midaflur
   1.875 g acepromazine maleate
   q.s. to 100.0 ml with vehicle system
8 - 10.0/5.0 mg/ml
   2.500 g midaflur
   1.250 g acepromazine maleate
   q.s. to 250.0 ml with vehicle system All of the above formulations described in Example 2 were administered intravenously at various doses to dogs. The results are summarized in Table II.

From Table II, it can be seen that side effects were reduced or eliminated when acepromazine maleate was administered intravenously with midaflur. A dose response with acepromazine maleate was noted wherein, by the criteria used in Example 2, a dose of 1.1 mg/kg was less effective and doses of 3.0 and 6.0 mg/kg were more effective. No differences in the elimination of side effects were noted between the 3.0 and 6.0 mg/kg doses of acepromazine maleate.

TABLE II

THE EFFECT OF VARIOUS CONCENTRATIONS OF MIDAFLUR/ACEPROMAZINE MALEATE I.V. ON INDUCTION TIME, SURGICAL PLANE, RECOVERY TIME AND SIDE EFFECTS

DOGS

| Formulation No. | 2,3 | 2,3 | 2,3 | 2,3 | 2,3 | 2,3 | 2,3 | 2,3 | 2,3 | 2,3 | 2,3 | 2,3 | 2,3 | 2,3 | 2,3 | 2,3 | 2,3 | 2,3 | 2,3 | 2,3 | 2,3 |
|---|---|---|---|---|---|---|---|---|---|---|---|---|---|---|---|---|---|---|---|---|---|
| Midaflur | | | | | | | | | | | | | | | | | | | | | |
| Dose (mg/kg) | 2.0 | 2.0 | 4.0 | 4.0 | 4.0 | 4.0 | 4.0 | 4.0 | 6.0 | 6.0 | 6.0 | 6.0 | 6.0 | 6.0 | 6.0 | 6.0 | 6.0 | 6.0 | 6.0 | 6.0 | 6.0 |
| Concentration (mg/ml) | 20.0 | 20.0 | 20.0 | 20.0 | 20.0 | 20.0 | 20.0 | 20.0 | 20.0 | 20.0 | 20.0 | 20.0 | 20.0 | 20.0 | 20.0 | 20.0 | 20.0 | 20.0 | 20.0 | 20.0 | 20.0 |
| Acepromazine Maleate | | | | | | | | | | | | | | | | | | | | | |
| Dose (mg/kg) | 1.1 | 1.1 | 1.1 | 0.75 | 1.1 | 1.1 | 1.1 | 1.1 | 1.1 | 1.1 | 1.1 | 1.65 | 1.65 | 1.65 | 1.65 | 1.65 | 1.65 | 1.65 | 1.65 | 1.65 | 2.0 |
| Concentration (mg/ml) | 5.0 | 5.0 | 5.0 | 5.0 | 5.0 | 5.0 | 5.0 | 5.0 | 5.0 | 5.0 | 5.0 | 5.0 | 5.0 | 5.0 | 5.0 | 5.0 | 5.0 | 5.0 | 5.0 | 5.0 | 5.0 |
| Induction Time (min) | 2 | 2 | 2 | 2-4 | 2 | 2 | 2 | 2 | 2 | 2 | 2 | 2 | 2 | 2 | 2 | 2 | 2 | 2 | 2 | 2 | 2 |
| Surgical Plane (min) | 30 | 20 | 45 | ≈45 | 30 | 45 | 35 | 45 | 80 | 60 | 40 | 40 | 60 | 30 | 60 | 100 | 40 | 45 | 30 | 45 | 45 |
| Recovery (min) | 45 | 26 | 65 | 75 | 75 | 115 | 205 | 55 | 103 | 129 | 160 | 137 | 145 | 150 | 254 | 145 | 145 | 210 | 92 | 102 | 120 |
| Side Effects | | | | | | | | | | | | | | | | | | | | | |
| A. Running Movements | 1 | 1 | 0 | 1 | 1 | 0 | 0 | 0 | 3 | 0 | 1 | 0 | 2 | 0 | 0 | 1 | 2 | 0 | 0 | 0 | 0 |
| B. Vocalization | 1 | 0 | 1 | 0 | 0 | 0 | 0 | 0 | 1 | 0 | 0 | 1 | 0 | 1 | 0 | 0 | 0 | 0 | 0 | 0 | 0 |

| Formulation No. | 2,3 | 2,3 | 2,4 | 2,4 | 2,4 | 2,4 | 2,4 | 2,4 | 2,4 | 7 | 7 | 7 | 7 | 7 | 7 | 7 | 7 | 7 | 7 | 7 | 7 |
|---|---|---|---|---|---|---|---|---|---|---|---|---|---|---|---|---|---|---|---|---|---|
| Midaflur | | | | | | | | | | | | | | | | | | | | | |
| Dose (mg/kg) | 6.0 | 6.0 | 6.0 | 6.0 | 6.0 | 6.0 | 6.0 | 6.0 | 6.0 | 6.0 | 6.0 | 6.0 | 6.0 | 6.0 | 6.0 | 6.0 | 6.0 | 6.0 | 6.0 | 6.0 | 6.0 |
| Concentration (mg/ml) | 20.0 | 20.0 | 20.0 | 20.0 | 20.0 | 20.0 | 20.0 | 20.0 | 20.0 | 37.5 | 37.5 | 37.5 | 37.5 | 37.5 | 37.5 | 37.5 | 37.5 | 37.5 | 37.5 | 37.5 | 37.5 |
| Acepromazine Maleate | | | | | | | | | | | | | | | | | | | | | |
| Dose (mg/kg) | 2.5 | 2.5 | 2.5 | 2.5 | 2.5 | 2.5 | 2.5 | 2.5 | 2.5 | 3.0 | 3.0 | 3.0 | 3.0 | 3.0 | 3.0 | 3.0 | 3.0 | 3.0 | 3.0 | 3.0 | 3.0 |
| Concentration (mg/ml) | 5.0 | 10.0 | 10.0 | 10.0 | 10.0 | 10.0 | 10.0 | 10.0 | 10.0 | 18.75 | 18.75 | 18.75 | 18.75 | 18.75 | 18.75 | 18.75 | 18.75 | 18.75 | 18.75 | 18.75 | 18.75 |
| Induction Time (min) | 2 | 2 | 2 | 2 | 2 | 2 | 2-10 | 2 | 2 | 2 | 2 | 2 | 2 | 2 | 2 | 2-5 | 2 | 2 | 5 | 2 | 2 |
| Surgical Plane (min) | 150 | 30 | 30 | 60 | 75 | 30 | ≈45 | 60 | 30 | 60 | 30 | 75 | 60 | 30 | 30 | ≈10 | 45 | 30 | 45 | 60 | 45 |
| Recovery (min) | 205 | 118 | 313 | 124 | 140 | 135 | 145 | 280 | 405 | >450 | 259 | >420 | 150 | 254 | 231 | 123 | >452 | 185 | 185 | >450 | >463 |
| Side Effects | | | | | | | | | | | | | | | | | | | | | |
| A. Running Movements | 0 | 0 | 0 | 0 | 0 | 0 | 0 | 0 | 0 | 0 | 0 | 0 | 0 | 0 | 0 | 0 | 0 | 0 | 0 | 0 | 0 |
| B. Vocalization | 1 | 0 | 1 | 1 | 0 | 0 | 0 | 0 | 0 | 0 | 1 | 1 | 1 | 0 | 0 | 0 | 0 | 0 | 0 | 0 | 0 |

| Formulation No. | 5 | 5 | 5 | 8 | 8 | 8 | 8. | 6 | 6 | 6 | 5 | 5 | 5 | 5 | 6 | 6 | 6 | 6 | 7 | 7 | 7 |
|---|---|---|---|---|---|---|---|---|---|---|---|---|---|---|---|---|---|---|---|---|---|
| Midaflur | | | | | | | | | | | | | | | | | | | | | |
| Dose (mg/kg) | 6.0 | 6.0 | 6.0 | 6.0 | 6.0 | 6.0 | 6.0 | 6.0 | 6.0 | 6.0 | 6.0 | 6.0 | 6.0 | 6.0 | 6.0 | 6.0 | 6.0 | 6.0 | 6.0 | 6.0 | 6.0 |
| Concentration (mg/ml) | 75.0 | 75.0 | 75.0 | 10.0 | 10.0 | 10.0 | 10.0 | 37.5 | 37.5 | 37.5 | 75.0 | 75.0 | 75.0 | 75.0 | 37.5 | 37.5 | 37.5 | 37.5 | 37.5 | 37.5 | 37.5 |
| Acepromazine Maleate | | | | | | | | | | | | | | | | | | | | | |
| Dose (mg/kg) | 3.0 | 3.0 | 3.0 | 3.0 | 3.0 | 3.0 | 3.0 | 6.0 | 6.0 | 6.0 | 3.0 | 3.0 | 3.0 | 3.0 | 6.0 | 6.0 | 6.0 | 6.0 | 3.0 | 3.0 | 3.0 |
| Concentration (mg/ml) | 37.5 | 37.5 | 37.5 | 37.5 | 37.5 | 37.5 | 37.5 | 37.5 | 37.5 | 37.5 | 37.5 | 37.5 | 37.5 | 37.5 | 37.5 | 37.5 | 37.5 | 37.5 | 18.75 | 18.75 | 18.75 |
| Induction Time (min) | 2 | 2 | 2 | 2 | 2 | 2 | 2 | 2 | 2 | 2 | 2 | 2 | 2 | 2 | 2-5 | 2 | 2 | 2 | 2 | 2 | 2 |
| Surgical Plane (min) | 45 | 30 | 30 | 35 | 30 | 10 | 75 | 30 | 45 | 60 | 90 | 60 | 30 | 30 | ≈10 | 20 | 45 | 60 | 45 | 60 | 45 |
| Recovery (min) | 249 | 231 | 372 | >402 | 313 | >390 | >390 | 120 | 145 | >450 | 259 | 135 | 150 | 254 | 123 | 90 | 122 | 333 | 185 | >450 | 262 |
| Side Effects | | | | | | | | | | | | | | | | | | | | | |
| A. Running Movements | 0 | 0 | 0 | 0 | 0 | 0 | 0 | 0 | 0 | 0 | 0 | 0 | 0 | 0 | 0 | 0 | 0 | 0 | 0 | 0 | 0 |
| B. Vocalization | 0 | 0 | 0 | 0 | 0 | 0 | 0 | 1 | 0 | 0 | 0 | 0 | 0 | 0 | 0 | 0 | 0 | 0 | 0 | 0 | 0 |

| Formulation No. | 7 | 7 | 8 | 8 | 8 | 8 | 8 | 8 | 8 | 8 |
|---|---|---|---|---|---|---|---|---|---|---|
| Midaflur | | | | | | | | | | |
| Dose (mg/kg) | 6.0 | 6.0 | 6.0 | 6.0 | 6.0 | 6.0 | 6.0 | 6.0 | 6.0 | 6.0 |
| Concentration (mg/ml) | 37.5 | 37.5 | 10.0 | 10.0 | 10.0 | 10.0 | 10.0 | 10.0 | 10.0 | 10.0 |
| Acepromazine Maleate | | | | | | | | | | |
| Dose (mg/kg) | 3.0 | 3.0 | 3.0 | 3.0 | 3.0 | 3.0 | 3.0 | 3.0 | 3.0 | 3.0 |

TABLE II-continued

THE EFFECT OF VARIOUS CONCENTRATIONS OF MIDAFLUR/ACEPROMAZINE MALEATE I.V. ON INDUCTION TIME, SURGICAL PLANE, RECOVERY TIME AND SIDE EFFECTS — DOGS

| Concentration (mg/ml) | 18.75 | 18.75 | 18.75 | 5.0 | 5.0 | 5.0 | 5.0 | 5.0 | 5.0 | 18.75 | 18.75 | 18.75 | 37.5 | 5.0 | 5.0 | 5.0 | 5.0 | 5.0 | 5.0 |
|---|---|---|---|---|---|---|---|---|---|---|---|---|---|---|---|---|---|---|---|
| Induction Time (min) | 2 | 2 | 2 | 2-10 | 2 | 2 | 2 | 2 | 2 | 4 | 2 | 2 | 3 | 2 | 2 | 1 | 3 | 1.5 | 2 |
| Surgical Plane (min) | 75 | 120 | 45 | ≈30 | ≈30 | 30 | 30 | 60 | 30 | 30 | 30 | 30 | 60 | 45 | 45 | 45 | 75 | ≈120 | 30 |
| Recovery (min) | >420 | >420 | 254 | >420 | >420 | 235 | 225 | >410 | >400 | 145 | 222 | 363 | 115 | 311 | 309 | 344 | 333 | >32' |
| Side Effects |  |  |  |  |  |  |  |  |  |  |  |  |  |  |  |  |  |  |  |
| A. Running Movements | 0 | 0 | 0 | 0 | 0 | 1 | 0 | 0 | 0 | 0 | 0 | 0 | 0 | 0 | 0 | 0 | 0 | 0 |
| B. Vocalization | 0 | 0 | 0 | 0 | 0 | 0 | 0 | 0 | 0 | 0 | 0 | 0 | 0 | 0 | 0 | 0 | 0 | 0 |

| Formulation No. | 2,3 | 2,3 | 2,4 | 2,4 | 2,4 | 2,4 | 2,4 |
|---|---|---|---|---|---|---|---|
| Midaflur |  |  |  |  |  |  |  |
| Dose (mg/kg) | 8.0 | 8.0 | 8.0 | 8.0 | 8.0 | 8.0 | 8.0 |
| Concentration (mg/ml) | 20.0 | 20.0 | 20.0 | 20.0 | 20.0 | 20.0 | 20.0 |
| Acepromazine Maleate |  |  |  |  |  |  |  |
| Dose (mg/kg) | 1.1 | 1.1 | 2.5 | 2.5 | 2.5 | 2.5 | 2.5 |
| Concentration (mg/ml) | 5.0 | 5.0 | 10.0 | 10.0 | 10.0 | 10.0 | 10.0 |
| Induction Time (min) | 2 | 4 | 2 | 2 | 2 | 2 | 2 |
| Surgical Plane (min) | 150 | 75 | 60 | 75 | 120 | 75 | 60 |
| Recovery (min) | 300 | 283 | 167 | 175 | 200 | 195 | 105 |
| Side Effects |  |  |  |  |  |  |  |
| A. Running Movements | 2 | 0 | 0 | 0 | 1 | 1 | 1 |
| B. Vocalization | 0 | 0 | 0 | 0 | 0 | 0 | 0 |

Side effects refer to those side effects that occur from induction time until the end of the surgical plane where:
0 = none
1 = minimal, occurred during less than ¼ of the surgical plane
2 = moderate, occurred during ¼ to ½ of the surgical plane
3 = maximal, occurred during greater than ½ of the surgical plane

EXAMPLE 3

Eight different formulations (9–16) containing midaflur and acepromazine maleate were prepared. The preparation and components of Formulations 9 through 16 are represented below:

Formulation

9. Midaflur 10.0 mg/ml
   Acepromazine maleate 5.0 mg/ml
   In a vehicle system consisting of equal parts of ethanol, propylene glycol, and distilled water. Filter sterilized.
10. Midaflur 10.0 mg/ml
    Acepromazine maleate 1.0 mg/ml
    In a vehicle system consisting of equal parts of ethanol, propylene glycol, and distilled water. Filter sterilized.
11. Midaflur 20.0 mg/ml
    Acepromazine maleate 2.0 mg/ml
    In a vehicle system consisting of equal parts of ethanol, propylene glycol, and distilled water. Filter sterilized.
12. Midaflur 20.0 mg/ml
    J Acepromazine maleate 0.40 mg/ml
    In a vehicle system consisting of equal parts of ethanol, propylene glycol, and distilled water. Filter sterilized.
13. Midaflur 10.0 mg/ml
    Acepromazine maleate 0.20 mg/ml
    In a vehicle system consisting of equal parts of ethanol, propylene glycol, and distilled water. Filter sterilized.
14. Midaflur 20.0 mg/ml
    Acepromazine maleate 0.20 mg/ml
    In a vehicle system consisting of equal parts of ethanol, propylene glycol, and distilled water. Filter sterilized.
15. Midaflur 10.0 mg/ml
    Acepromazine maleate 0.10 mg/ml
    In a vehicle system consising of equal parts of ethanol, propylene glycol, and distilled water. Filter sterilized.
16. Midaflur 20.0 mg/ml
    Acepromazine maleate 0.10 mg/ml
    In a vehicle system consisting of equal parts of ethanol, propylene glycol, and distilled water. Filter sterilized.

All of the above formulations described in Example 3 were administered intraveneously at various doses to dogs.

The number of dogs tested with each formulation is as follows:

| Formulation | Number of Dogs |
| --- | --- |
| 9 | 14 |
| 10,11 | 23 |
| 12,13 | 61 |
| 14,15 | 20 |
| 16 | 10 |

The results are summarized in Tables III and IV. Tables III and IV show that the side effects were reduced or eliminated when acepromazine maleate was administered intraveneously with midaflur at ratios as low as two hundred to one. A dose response with acepromazine maleate was noted with doses ranging from 0.025 mg/kg to 2.5 mg/kg.

TABLE III

THE EFFECT OF VARIOUS MIDAFLUR/ACEPROMAZINE MALEATE DOSES ON INDUCTION TIME, SURGICAL PLANE, AND RECOVERY TIME WHEN ADMINISTERED I.V. TO DOGS

| FORMULATION NUMBER | 9 | 10,11 | 12,13 | 14,15 | 16 |
| --- | --- | --- | --- | --- | --- |
| RATIO OF MIDAFLUR/ ACEPROMAZINE MALEATE | 2/1 | 10/1 | 50/1 | 100/1 | 200/1 |
| MIDAFLUR DOSE (MG/KG) | 5.0 | 5.0 | 5.0 | 5.0 | 5.0 |
| ACEPROMAZINE MALEATE DOSE (MG/KG) | 2.5 | 0.5 | 0.1 | 0.05 | 0.025 |
| INDUCTION TIME (Mean) (minutes) | 2.0 | 2.4 | 3.0 | 3.0 | 2.9 |
| SURGICAL PLANE (Mean) (minutes) | 51.9 | 35.5[a] | 32.1 | 27.9 | 30.0 |
| RECOVERY TIME (Mean) (minutes) | 175.3 | 128.0[b] | 129.5[b] | 85.0[c] | 65.9[c] |

[a] = Two of the 23 dogs did not attain a surgical plane.
[b] = Does not include 1 dog with a 5–24 hour recovery time.
[c] = Does not include 2 dogs with a 5–24 hour recovery time.

TABLE IV

THE EFFECT OF VARIOUS MIDAFLUR/ACEPROMAZINE MALEATE DOSES ON SIDE EFFECTS DURING INDUCTION (I), SURGICAL PLANE (SP), AND RECOVERY (R) WHEN ADMINISTERED I.V. TO DOGS

| FORMULATION NO. | 9 | | | 10,11 | | | 12,13 | | | 14,15 | | | 16 | | |
| --- | --- | --- | --- | --- | --- | --- | --- | --- | --- | --- | --- | --- | --- | --- | --- |
| RATIO OF MIDAFLUR/ ACEPROMAZINE MALEATE | 2/1 | | | 10/1 | | | 50/1 | | | 100/1 | | | 200/1 | | |
| MIDAFLUR DOSE (MG/KG) | 5.0 | | | 5.0 | | | 5.0 | | | 5.0 | | | 5.0 | | |
| ACEPROMAZINE MALEATE (MG/KG) | 2.5 | | | 0.5 | | | 0.1 | | | 0.05 | | | 0.025 | | |
| STAGES OF ANESTHESIA | I | SP | R | I | SP | R | I | SP | R | I | SP | R | I | SP | R |
| SIDE EFFECTS (% of dogs affected) | | | | | | | | | | | | | | | |
| RUNNING MOVEMENTS | | | | | | | | | | | | | | | |
| None | 57 | 100 | 50 | 43 | 76 | 29 | 61 | 74 | 23 | 45 | 50 | 10 | 40 | 40 | 10 |
| Not Significant[a] | 43 | 0 | 43 | 48 | 24 | 62 | 28 | 25 | 70 | 25 | 50 | 75 | 40 | 60 | 70 |
| Significant[b] | 0 | 0 | 14 | 33 | 0 | 19 | 16 | 0 | 18 | 50 | 10 | 45 | 60 | 20 | 40 |
| VOCALIZATION | | | | | | | | | | | | | | | |
| None | 79 | 100 | 64 | 86 | 100 | 86 | 75 | 98 | 70 | 75 | 95 | 90 | 60 | 90 | 80 |
| Not Significant[c] | 14 | 0 | 36 | 10 | 0 | 10 | 20 | 2 | 20 | 20 | 5 | 5 | 30 | 10 | 10 |

TABLE IV-continued
THE EFFECT OF VARIOUS MIDAFLUR/ACEPROMAZINE MALEATE DOSES ON SIDE EFFECTS DURING INDUCTION (I), SURGICAL PLANE (SP), AND RECOVERY (R) WHEN ADMINISTERED I.V. TO DOGS

| Significant[d] | 7 | 0 | 7 | 5 | 0 | 10 | 5 | 0 | 16 | 5 | 0 | 5 | 10 | 0 | 10 |
|---|---|---|---|---|---|---|---|---|---|---|---|---|---|---|---|

[a] = Running movements that are not signigicant are muscle twitches and slight running movements.
[b] = Running movements that are significant are moderate and strong running movements.
[c] = Vocalization that is not significant is quiet vocalization.
[d] = Vocalization that is significant is loud vocalization.

What is claimed is:

1. An injectable anesthetic composition comprising from about 0.025 mg/kg to about 6.0 mg/kg of mammal body weight of acepromazine, or a pharmaceutically acceptable salt thereof, and midaflur wherein the ratio of midaflur to acepromazine is about two hundred to one to about one to one, in a pharmaceutically acceptable liquid vehicle.

2. A composition according to claim 1 wherein the ratio of midaflur to acepromazine is about one hundred to one to about two to one and acepromazine is present in amounts from about 0.05 mg/kg to about 2.5 mg/kg.

3. A composition according to claim 1 wherein the acepromazine is the maleate salt.

4. The composition according to claim 1 wherein midaflur and acepromazine maleate is present in amounts of about 10.0-20.0/0.2-0.4 mg/ml.

5. A method of inducing anesthesia in a mammal which comprises administering intravenously to said mammal an amount sufficient to produce a surgical plane of anesthesia of acepromazine, or a pharmaceutically acceptable salt thereof, and midaflur together or separately at approximately the same time, the ratio of midaflur to acepromazine being between about two hundred to one and about one to one.

6. The method of claim 5 wherein the acepromazine is the maleate salt.

7. The method of claim 5 wherein the acepromazine and the midaflur are administered as the composition of claim 2.

* * * * *